(12) United States Patent
O'Kennedy (10) Patent No.: US 10,813,968 B2
(45) Date of Patent: Oct. 27, 2020

(54) METHOD OF TREATING A HUMAN SUFFERING FROM POST EXERCISE MUSCLE SORENESS

(71) Applicant: Provexis Natural Products Limited, Reading (GB)

(72) Inventor: Niamh O'Kennedy, Reading (GB)

(73) Assignee: Provexis Natural Products Limited, Reading (GB)

( * ) Notice: Subject to any disclaimer, the term of this patent is extended or adjusted under 35 U.S.C. 154(b) by 0 days.

(21) Appl. No.: 16/053,099

(22) Filed: Aug. 2, 2018

(65) Prior Publication Data

US 2019/0175681 A1 Jun. 13, 2019

Related U.S. Application Data

(63) Continuation of application No. 14/651,075, filed as application No. PCT/GB2013/053431 on Dec. 24, 2013, now abandoned.

(30) Foreign Application Priority Data

Dec. 24, 2012 (GB) .................................. 1223365.6

(51) Int. Cl.
| | |
|---|---|
| A61K 36/81 | (2006.01) |
| A23L 33/105 | (2016.01) |
| A23L 33/15 | (2016.01) |
| A23L 33/16 | (2016.01) |
| A61K 31/525 | (2006.01) |
| A61K 9/00 | (2006.01) |
| A61K 9/06 | (2006.01) |
| A61K 9/20 | (2006.01) |
| A61K 31/519 | (2006.01) |
| A61K 36/21 | (2006.01) |

(52) U.S. Cl.
CPC ............ *A61K 36/81* (2013.01); *A23L 33/105* (2016.08); *A23L 33/15* (2016.08); *A23L 33/16* (2016.08); *A61K 9/009* (2013.01); *A61K 9/0053* (2013.01); *A61K 9/06* (2013.01); *A61K 9/20* (2013.01); *A61K 31/519* (2013.01); *A61K 31/525* (2013.01); *A61K 36/21* (2013.01); *A23V 2002/00* (2013.01); *A23V 2200/33* (2013.01)

(58) Field of Classification Search
CPC ...................................................... A61K 36/00
USPC ......................................................... 424/725
See application file for complete search history.

(56) References Cited

U.S. PATENT DOCUMENTS

| | | |
|---|---|---|
| 4,925,690 A | 5/1990 | Odake |
| 5,502,038 A | 3/1996 | Malinow |
| 6,436,452 B1 | 8/2002 | Deutz et al. |
| 6,780,444 B1 | 8/2004 | Reza |
| 6,958,164 B2 | 10/2005 | Dutta-Roy |
| 2003/0206983 A1 | 11/2003 | Dutta-Roy |
| 2004/0191790 A1 | 9/2004 | Tomassen et al. |
| 2004/0223962 A1 | 11/2004 | Riordan |
| 2005/0153038 A1 | 6/2005 | Giori |
| 2006/0035971 A1 | 2/2006 | Youichi et al. |
| 2006/0078632 A1 | 4/2006 | Woo et al. |
| 2006/0084614 A1 | 4/2006 | Eckl et al. |
| 2006/0154877 A1 | 7/2006 | Liu et al. |
| 2007/0082071 A1 | 4/2007 | Willimann |
| 2007/0259059 A1 | 11/2007 | Eidenberger |
| 2008/0009449 A1 | 1/2008 | Prasad |
| 2009/0053340 A1 | 2/2009 | Crosbie et al. |
| 2009/0123584 A1 | 5/2009 | O'Kennedy |
| 2011/0206794 A1 | 8/2011 | O'Kennedy |
| 2011/0212913 A1 | 9/2011 | O'Kennedy |
| 2012/0321732 A1 | 12/2012 | O'Kennedy |
| 2013/0023489 A1 | 1/2013 | Kubow et al. |
| 2014/0147537 A1 | 5/2014 | O'Kennedy |
| 2015/0105338 A1 | 4/2015 | O'Kennedy |
| 2015/0132371 A1 | 5/2015 | Duttaroy |
| 2016/0375080 A1 | 12/2016 | O'Kennedy |
| 2018/0256666 A1 | 9/2018 | O'Kennedy |
| 2018/0271926 A1 | 9/2018 | Duttaroy |
| 2020/0054706 A1 | 2/2020 | Mussler et al. |

FOREIGN PATENT DOCUMENTS

| | | |
|---|---|---|
| CN | 1352941 | 6/2002 |
| CN | 1650951 | 8/2005 |
| DE | 19720767 A1 | 11/1998 |
| EP | 1334728 A2 | 8/2003 |
| EP | 1481669 A1 | 12/2004 |
| EP | 1508325 A1 | 2/2005 |
| EP | 1559421 A1 | 8/2005 |
| EP | 1640001 A1 | 3/2006 |
| EP | 2036568 A1 | 3/2009 |
| FR | 2871378 A1 | 12/2005 |
| JP | 050201846 | 8/1993 |
| JP | H09-009892 A | 1/1997 |

(Continued)

OTHER PUBLICATIONS

Exam Report of EP Application No. 07733050.4, dated Jan. 13, 2012, 7 pages.

(Continued)

*Primary Examiner* — Michael V Meller (74) *Attorney, Agent, or Firm* — Linda B. Huber; Nixon Peabody LLP (57) ABSTRACT

The present invention relates to the use of a fruit extract and optionally other specific nutrients for preventing, reducing or minimising exercise-induced systemic inflammation and/or for promoting recovery from intense exercise. The invention also relates to compositions comprising such fruit extracts.

4 Claims, 5 Drawing Sheets

(56) References Cited

FOREIGN PATENT DOCUMENTS

| | | |
|---|---|---|
| JP | 03004769 | 1/1999 |
| JP | 2004-137287 A | 5/2004 |
| JP | 2004315386 A | 11/2004 |
| JP | 2006193435 A | 7/2006 |
| JP | 2007037530 A | 2/2007 |
| JP | 2009240191 A | 10/2009 |
| WO | 94/03421 | 2/1994 |
| WO | 99/55350 A1 | 11/1999 |
| WO | 00/21507 A2 | 4/2000 |
| WO | 2006085115 | 8/2006 |
| WO | 06/094120 A2 | 9/2006 |
| WO | 07/141495 A1 | 12/2007 |
| WO | 08/080162 A2 | 7/2008 |
| WO | 08/131047 A2 | 10/2008 |
| WO | 2010/049707 A2 | 5/2010 |
| WO | 2010/049709 A2 | 5/2010 |
| WO | 2013/163057 A1 | 10/2013 |
| WO | 2014/102546 A1 | 7/2014 |
| WO | 2018083137 A1 | 5/2018 |

OTHER PUBLICATIONS

Kagome. Antihypertensive food having tomato flavour—plus contains serosity tomato juice which suppresses hypertension caused by angiotensin converting enzyme. Database WPI—Publication No. JP H09 9892 A (Jan. 14, 1997). 1 page. Abstract Only.

Talbott et al. Ironman Triathlon Recovery Enhanced by Dietary Supplementation. FASEB Journal (2007). 21(5). 1 page. Abstract Only.

Lidder et al. Vascular effects of dietary intrate (as found in green leafy vegetables and beetroot) via the nitrate-nitrite-nitric oxide pathway. British Journal of Clinical Pharmacology (2012). 75(3):677-696.

Cermak et al. Nitrate Supplemantation's Improvement of 10-km-Time-Trial Performance in Trained Cyclists. International Journal of Sport Nutrition and Exercise Metabolism (2012). 22:84-91.

Murphy et al. Whole Beetroot Consumption Actutely Improves Running Performance. J Acad Nutr Diet (2012). 112:548-552.

Nieman et al. Effects of Quercetin and EGCG on Mitochondrial Biogenesis and Immunity. Med Sci Sports Exerc (2009). 41(7):1467-1475.

dietandfitnesstoday.com Tomatoes Folic Acid Content, downloaded from the internet on Oct. 30, 2017, 14 pages.

Kagome. An Agent used in foodstuffs and beverages for improving fatigue, comprises liquid squeezed from a tomato or component obtained by centrifuging squeezed tomato liquid. Database WPI for Publication No. JP 2006-193435 (2006). 1 page. Abstract Only.

Paran et al. The Effects of Natural Antioxidants from Tomato Extract in Treated but Controlled Hypertensive Patients. Cardiovasc Drugs Ther (2009). 23:145-151.

De Leeuw et al. Tomato Extract for Hypertension? Cardiovasc Drugs Ther (2009). 23:107-108.

Kloek et al. Effect of a Paste from Flavonoid-enriched Tomatoes on Blood Pressure in Spontaneously Hypertensive Rats. FASEB Journal (2004). 18(4-5). Abstract Only.

PCT/GB09/002595 IPRP dated May 12, 2011.

PCT/GB09/002595 International Search Report dated Apr. 26, 2010.

PCT/GB09/002595 Written Opinion dated May 12, 2011.

PCT/GB2006/000521 IPRP dated Aug. 14, 2007.

PCT/GB2006/000521 International Search Report dated Jul. 26, 2006.

PCT/GB2006/000521 Written Opinion dated Jul. 26, 2006.

PCT/GB2007/002034 IPRP dated Dec. 3, 2008.

PCT/GB2007/002034 International Search Report dated Oct. 19, 2007.

PCT/GB2007/002034 Written Opinion dated Oct. 19, 2007.

Abushita et al., Determination of Antioxidant Vitamins in Tomatoes. Food Chemistry (1997), 60(2):207-212.

Anton et al., Thermal inactivation of pectin methylesterase, polygalacturonase, and peroxidase in tomato juice. Journal of Agriculture and Food Chemistry (2002), 50:6153-6159.

Bohm et al., Intestinal absorption of lycopene from different matrices and interactions to other carotenoids, the lipid status, and the antioxidant capacity of human plasma. European Journal of Nutrition (1999), 38(2):1436-6207. Abstract Only.

Dutta-Roy et al., Effects of tomato extract on human platelet aggregation in vitro. Platelets (2001), 12(4):218-227.

Friedman et al., Feeding tomatoes to hamsters reduces their plasma low-density lipoprotein cholesterol and triglycerides. Journal of Food Science (2000), 65(5):897-900. Abstract Only.

Hsiao G. et al., Inhibitory effects of lycopene on in vitro platelet activation and in vivo prevention of thrombus formation. Journal of Laboratory and Clinical Medicine (2005), 146(4):216-226.

Lopez et al., Deep venous thrombosis. American Society of Hematology (2004), 439-456.

Maruyama et al. Therapeutic strategy targeting coagulation factor Xa in thromboemobolism—Antithrombotic therapy by targeting Xa. Journal of Clinical and Experimental Medicine (2004). 208:393-395.

O'Kennedy et al., Effects of antiplatelet components of tomato extract on platelet function in vitro and ex vivo: a time-course cannulation study in healthy humans. American Journal of Clinical Nutrition (2006), 84(3):570-579.

O'Kennedy et al., Effects of tomato extract on platelet function: a double-blinded crossover study in healthy humans. American Journal of Clinical Nutrition (2006), 84(3): 561-569.

Jerjes-Sanchez, C. Venous and arterial thrombosis: a continuous spectrum of the same disease? European Heart Journal. (2005) 26(1):3-4.

Van Het Hof et al., Carotenoid bioavailability in humans from tomatoes processed in different ways determined from the carotenoid response in the triglyceride-rich lipoprotein fraction of plasma after a single consumption and in plasma after four days of consumption. Journal of Nutrition (2000), 130:1189-1196.

Weber M. et al. Enhance platelet aggregation with TRAP-6 and collagen in platelet aggregometry in patients with venous thromboembolism Thrombosis Research. (2002) 107(6):325-328.

Yamamoto et al., Tomatoes have natural anti-thrombotic effects. British Journal of Nutrition (2003), 90(6):1031-1038.

Yokoyama et al. New anti-platelet drug and anticoagulation drug—Differences from aspen, warfarin and heparin. Journal of Clinical and Experimental Medicine (2006). Supp Vol (Apoplexy): 17-22.

Zhu T. et al. Three-Dimensional Reconstruction of Thrombus Formation during Photochemically Induced Arterial and Venous Thrombosis. Animals of Biomedical Engineering Society. (2003) 31(5):515-525.

Hwang et al., Effects of tomato paste extracts on cell proliferation, cell-cycle arrest and apoptosis in LNCaP human prostate cancer cells. BioFactors. 2005, 23:75-84.

Miean et al., Flavonoid (myricetin, quercetin, kaempferol, luteolin, and apigenin) content of edible tropical plants. Medicinal & Aromatic Plants Abstracts. 2002, 24(1).

Naczk et al., Pheolics in cereals, fruits and vegetables: Occurrence, extraction and analysis. Journal of Pharmaceutical and Biomedical Analysis. 2006, 41(5):1523-1542. Abstract.

Slimestad et al., Journal of Agricultural and Food Chemistry. 2008, 56(7):2436-2441.

Stevenson et al., Comparison of the relative recovery of polyphenolics in two fruit extracts from a model of degradation during digestion and metabolism. Molecular Nutrition & Food Research. 2007, 51(8):939-945.

Zheng et al., Oxygen radicals absorbing capacity of phenolics in blueberries, cranberries, chokeberries, and lingonberries. Journal of Agricultural and Food Chemistry. 2003, 51(2).

Oliff, H. Scientific and Clinical Monograph for Pycnogenol. Retrieved from internet: http://abc.herbalgram.org/site/DocServer/Pycnog_FullMono120809_LOW.pdf?docID=1741 on Jan. 1, 2010.

PCT/GB2009/002593 International Search Report and Written Opinion dated Aug. 10, 2011.

PCT/GB2009/002593 International Preliminary Report on Patentability dated Oct. 11, 2011.

(56) References Cited

OTHER PUBLICATIONS

Hua, J. Diagnosis and Treatment of Deep Venuous Thrombosis Formation in the Lower Limbs (with Analysis of 73 Cases). Zhejiang Medical Journal (1991). 13(6): 3-5.
Longo et al. Extract from Harrison's Principals of Internal Medicine. McGraw Hill Companies, Inc. 18th Edition (2012). 9 pages.
Martini et al. Extract from Fundamentals of Anatomy and Physiology. Blood (2009) 8th Edition. Ch. 11. pp. 262-263.
Roth, GJ. Platelets and blood vessels: the adhesion event. Immunology Today (1992). 13(3):100-105.
Zhuang, Q. Blood Coagulation and Fibrinolysis. Chinese Journal of Medicine (1981). 2(11):10-13.
Moco et al. A Liquid Chromatography-Mass Spectrometry-Based Metabolome Database for Tomato. Plant Physiology (2006). 141:1205-1218.
Chinese Patent Application No. 2007800204350 Examination Report.
PCT/GB2013/053431 International Search Report and Written Opinion dated Feb. 4, 2014; 11 pages.
PCT/GB2013/053431 International Preliminary Report on Patentability dated Jun. 30, 2015; 8 pages.
PCT/US2013/037524 International Search Report and Written Opinion dated Jul. 8, 2013; 11 pages.
PCT/US2013/037524 International Preliminary Report on Patentability dated Oct. 28, 2014; 8 pages.
GB Application No. 1223365.6 UKIPO Search Report dated Jun. 12, 2013; 2 pages.
Abbey et al. Effect of Quercetin Supplementation on Repeated-Sprint Performance, Xanthine Oxidase Activity, and Inflammation. International Journal of Sport Nutrition and Exercise Metabolism (2011). 91-96.
Amagase et al. Lycium barbarum Attenuates Increased Plasma Stress Hormone Levels Induced by a Short and Intense Exercise Challenge. A Randomized, Double-blind, Placebo-controlled Human Clinical Study. FASEB Journal (2009). 23: 2 pages. Abstract Only.
Burton-Freeman et al. Protective activity of processed tomato products on postprandial oxidation and Inflammation: A clinical trial in healthy weight men and women. Mol. Nutr. Food Res. (2012). 56:622-631.
Castell et al. Granule Localization of Glutaminase in Human Neutrophils and the Consequence of Glutamine Utilization for Neutrophil Activity. The Journal of Biological Chemistry (2004). 279(14):13305-13310.
International Search Report and Written Opinion of PCT/EP2017/077993, dated Jan. 23, 2018, 10 Pages.
Lucking et al., Diesel Exhaust Inhalation Increases Thrombus Formation in Man, 2008, European Heart Journal, vol. 29(24), pp. 3043-3051.
Chaouat et al., The Role of Thrombosis in Severe Pulmonary Hypertension, European Respiratory Journal, 1996, vol. 9, pp. 356-363.
Franklin, S.J., GRAS Exemption Claim: Claim of Exemption from the Requirement for Premarket Approval Pursuant to Proposed 21 CFR Section 170.36 (c)(1) [62 FR 18938 (Apr. 17, 1997) for Water-Soluable Tomato Concentrate (WSTC), Prepared by Provexis, 2006, 74 pages.
Siddesha et al., Inhibition of Angiotensin Converting Enzyme (ACE) by Medicinal Plants Exhibiting Antihypertensive Activity, Recent Progress in Medicinal Plants, 2010, vol. 29, pp. 269-308, Abstract.

METHOD OF TREATING A HUMAN SUFFERING FROM POST EXERCISE MUSCLE SORENESS

CROSS-REFERENCE TO RELATED APPLICATIONS

This application is a continuation of U.S. patent application Ser. No. 14/651,075 filed Jun. 10, 2015, which is the National Phase of International Application PCT/GB2013/053431, filed Dec. 24, 2013, which designated the United States and that International Application was published under PCT Article 21(2) in English. This application also includes a claim of priority under 35 U.S.C. § 119(a) and § 365(b) to British patent application No. GB 1223365.6 filed Dec. 24, 2012, the entirety of which is hereby incorporated by reference.

COMPOSITIONS

The present invention relates to a composition containing a fruit extract or combinations of fruit extracts and optionally other specific nutrients that may be used to prevent exercise-induced systemic inflammation and promote recovery from intense exercise.

Sustaining any exercise regime requires both psychological commitment and physical capacity.

The extent of ongoing physical capacity is largely determined (in the absence of sustained injury) by the resilience of the body to stresses put upon it by the exercise regime, that is, the speed of recovery from the effects of these stresses.

Recovery from exercise involves many physical processes. These include repair of damaged muscle tissue; replenishment of muscle glycogen stores; removal of byproducts of metabolism which accumulate in muscle or other tissues during exercise; and response to and down-regulation of inflammation which arises during exercise.

Some exercise-induced inflammation is necessary for full recovery. For example localized inflammatory signaling within muscle groups utilized during exercise helps to recruit leukocytes to sites of muscle damage and thereby helps the healing process.

However some types of exercise can induce systemic inflammation, which acts not as a spur to healing but as a detrimental, whole-body inflammatory burden that can, especially if sustained during repeated exercise sessions, reduce the body's capacity to recover and put some biological systems under unnecessary and potentially dangerous stress.

Any exercise modality can trigger this systemic inflammation if the intensity of exercise is sufficient. Intense exercise, by which we mean any exercise conducted at an intensity corresponding to greater than approximately 60% $VO_2$max, is accompanied very quickly by activation of the haemostatic system. The haemostatic system comprises platelets and coagulation factors and both platelets and coagulation factors are activated by exercise intensities greater than 60% $VO_2$max. Their activation results in generation of thrombin, release of procoagulant and proinflammatory circulating microparticles, activation of circulating leukocytes, activation of the vascular endothelium, reduction in available nitric oxide and associated vasodilation, and an increase in circulating inflammatory markers such as IL-6.

High levels of circulating IL-6 are linked with more intense post-exercise muscle soreness, and slower recovery from the preceding exercise session.

In the light of this the inventor has appreciated that agents able to reduce exercise-induced generation of IL-6 and associated inflammatory markers are of potential use in promoting recovery from exercise. However it has been established that not all agents that suppress the haemostatic system affect exercise-induced activation of platelets, coagulation and inflammatory marker generation. There are many known anti-platelet-aggregation agents that act at different stages of platelet production and action, for example aspirin (acetylsalicylic acid) which is the most widely used and studied. However, such antiplatelet drugs do not suppress exercise-induced activation of the haemostatic system. This has been shown in patients taking long-term antiplatelet therapy, and is the reason for prohibition of exercise among groups of patients who might otherwise benefit from a regular exercise regime. The main biological activators of platelets during intense exercise are thrombin and epinephrine, against which the most commonly used antiplatelet drugs have very limited efficacy. Thrombin and epinephrine working together present a very potent system for platelet activation, which is irreversible and very fast acting.

It is therefore an object of the present invention to identify a composition that will treat, reduce, minimise or prevent exercise-induced systemic inflammation in a subject and will therefore be useful for promoting recovery from exercise in a subject.

According to a first aspect of the invention there is provided a water-soluble extract of fruit of the Solanaceae family with activity for inhibiting platelet aggregation for use in treating, reducing, minimising or preventing exercise-induced systemic inflammation in a subject.

By "preventing" we mean the extract will stop exercise-induced inflammation from occurring or in the alternative will reduce the severity of the exercise-induced inflammation; delay on set of the exercise-induced inflammation; or lessen symptoms associated with exercise-induced inflammation.

By "reducing" we mean the extract will, when compared to a control subject who does not receive the extract, reduce the severity of the exercise-induced inflammation; delay on set of the exercise-induced inflammation; or lessen symptoms associated with exercise-induced inflammation.

By "minimising" we mean the exercise-induced inflammation will be reduced (even if not eliminated) to such an extent that it will not delay recovery from exercise in a subject.

In a preferred embodiment the use of the extract improves or promotes recovery from exercise in a subject (when compared to a control subject who does not receive the extract.

Recovery periods are necessary to allow the nervous, endocrine and musculoskeletal systems an opportunity to carry out vital repair work. The muscular system, for example, requires time to repair cells damaged during strenuous effort. Muscles also require time to metabolise nutrients, replenish glycogen stores and to synthesise new enzymes and energy-producing mitochondria. During recovery, the nervous system adapts to the stresses placed on it so that it can better control the specialised motor patterns used during training. The endocrine system must return to equilibrium. Increased inflammatory loading can interfere with these processes, reducing the extent of recovery during breaks from training, and potentially upsetting the balance between training and recovery which is essential for peak athletic performance.

According to a second aspect of the invention there is provided a water-soluble extract of fruit of the Solanaceae family with activity for inhibiting platelet aggregation for use in promoting recovery from exercise in a subject.

The inventor has found that most antiplatelet agents (e.g. aspirin) were ineffective for treating or preventing exercise-induced systemic inflammation in a subject or promoting recovery from exercise in a subject. She was therefore surprised to find that a known water-soluble tomato extract with antiplatelet activity (disclosed in International Patent application WO 99/55350 with inventive refinements described in WO 2010/049707) did show efficacy in reducing exercise-induced inflammation as defined by endothelial IL-6 production under conditions simulating intense exercise.

WO 2010/049707 discloses a method of producing water-soluble tomato extract with optimal antiplatelet activity. Such water-soluble extracts were found in human trials to have significant efficacy for preventing or reducing platelet aggregation in response to adenosine diphosphate and collagen, and have been marketed, with a European Food Safety Authority authorised health claim in Europe, as a nutritional supplement with health benefits in the cardiovascular area.

The new data generated by the inventor (see the Examples) indicate that water-soluble tomato extracts (e.g. made as disclosed in WO 2010/049707), particularly when taken before intense exercise commences, also reduces exercise recovery times and improves quality of recovery after intense exercise.

It will be appreciated that the prevention of exercise-induced systemic inflammation will improve the ability of a subject to recover from intense exercise.

It is preferred that the fruit extract is used to promote recovery from intense exercise. By "intensive exercise" we mean any exercise conducted at an intensity corresponding to greater than approximately 60% $VO_2$max.

The fruit extract may be given to any mammalian subject and has utility in treating animals of veterinary interest (e.g. to improve the recovery of horses after exercise or a race). However it is preferred that the subject is a human subject and more preferred that the subject is a human subject that is about to undergo or has just undertaken intense exercise as defined above. The inventor has found that the extracts have most efficacy when given to physically fit individuals and particularly trained athletes or "elite" athletes who wish an optimal recovery from intense exercise.

The fruit extract is preferably an active water-soluble tomato extract (WSTC), the fraction containing a substantially heat stable colourless water soluble compound or compounds with activity for preventing platelet aggregation having a molecular weight of less than 1000.

The extract may be derived from the flesh of a peeled fruit and/or the juice surrounding the pips of a fruit.

The extracts may essentially comprise the juice of the fruit and that juice may then be further processed as discussed herein and in WO 99/55350 or WO 2010/049707.

The extract may be an active fraction which is isolatable from tomato and is preferably characterised in that it:
 (a) is colourless or straw-coloured;
 (b) is a water soluble compound;
 (c) consists of components having a molecular weight of less than 1000; and
 (d) contains one or more nucleosides having platelet aggregation inhibiting activity.

Preferred fruit extracts comprise:
 (a) a glycosylated phenolic acid or a phenolic ester, or derivatives thereof;
 (b) a glycosylated flavonoid; and
 (c) a nucleoside.

The glycosylated phenolic acid or phenolic ester may be a glycosylated cinnamic acid or derivative thereof. Such a glycosylated cinnamic acid or derivative thereof may be selected from the group comprising Caffeoyl-4-O-quinic acid, Caffeoyl-4-O-glucoside, Coumaroyl-4-O-glycoside (glue/gal) and Coumaroyl-4-O-glycoside (disaccharide).

The glycosylated phenolic acid or phenolic ester may be selected from: Caffeic acid glucoside; p-Coumaric acid hexose/dihydrokaempferol hexose; Ferulic acid glycoside; and a p-Coumaric acid derivative.

The glycosylated flavonoid may be Quercetin-3-O-glucoside or Rutin.

The nucleoside may be selected from the group comprising AMP, Uridine, Adenosine, Guanosine or GMP.

In most preferred embodiments the extract is any extract with activity for preventing platelet aggregation that is disclosed in WO 99/55350 or WO 2010/049707.

WO 99/55350, and particularly WO 2010/049707, also disclose preferred methods for manufacturing extracts that may be used according to the present invention.

WO 2010/049707 discloses most preferred methods for producing extracts, and extracts per se that may be used according to the present invention, in FIG. 2 (methods for making a liquid/syrup extract from the fruit) and FIG. 4 (methods of processing the extract to make a powder with sugars removed therefrom). These extracts, and the methods of manufacturing them, are incorporated herein by reference.

The inventor conducted further development work to produce novel compositions comprising water-soluble tomato extracts and a nitrate capable of conversion to exogenous nitric oxide by biological tissues.

The inventor was surprised to find that a combination of the fruit extract, with the nitrate was particularly useful according to the first or second aspects of the invention. The inventor does not wish to be bound by any hypothesis but believes this combination is effective because it not only targets platelet activation by thrombin and epinephrine, but also provides an exogenous source of nitric oxide for the platelets and endothelial cells to use if endogenous sources became depleted.

Extracts supplemented with nitrate represent an important feature of the invention. Therefore according to a third aspect of the invention there is provided a composition comprising:
 (a) a water-soluble extract of fruit of the Solanaceae family with activity for inhibiting platelet aggregation, wherein the extract comprises:
  (i) components having a molecular weight of less than 1000; and
  (ii) contains one or more of a nucleoside; a glycosylated phenolic acid or a phenolic ester, or derivative thereof; or a glycosylated flavonoid with platelet aggregation inhibiting activity;
and
 (b) a source of dietary nitrate or a precursor of endogenous nitric oxide.

The extract (a) in the composition of the third aspect of the invention may be any water-soluble extract of fruit of the Solanaceae family with activity for inhibiting platelet aggregation. Preferably the extract is one defined above and in particular one disclosed in WO 99/55350 or WO 2010/049707.

Sources of dietary nitrate (b) suitable for use in the composition according to this aspect of the invention include water-based extracts of fresh fruit or vegetable tissue, where the fruit or vegetable selected is known to contain levels of nitrate sufficiently high to result in final extract concentrations greater than 7.5 g/l or about 7.5 g/l nitrate. Examples of such fruit and vegetables include leafy green vegetables, for example the leaves of spinach, rocket, lettuce, chard, watercress; cruciferous vegetables such as cabbage or kale; fruits such as strawberry, apple or rhubarb The sources of dietary nitrate may be freshly prepared from fresh or freeze-dried fruit or vegetable tissues, or may be sourced from commercially available commodity products such as fruit and vegetable juice concentrates. Such concentrates may be standardised for nitrate content, by titring the dose used depending on nitrate content present. Alternatively dietary nitrates may be prepared by macerating fresh plant tissue after addition of water; removal of pulp by centrifugation or filtration; and concentration at low temperature to avoid degradation of nitrate for example by freeze drying, by low-temperature vacuum drying, or by low-temperature evaporation. It will be appreciated that the nitrate content of such preparations may also be standardised.

Sources of dietary nitrate may be used singly, or combinations from different sources materials may be prepared. Examples of preferred combinations are Swiss chard extract and rhubarb extract, or strawberry extract, rhubarb extract and lettuce extract.

Sources of dietary nitrate may be used either in liquid form or after removal of water by drying, in powder form. The final concentration of nitrate present in the final form of the source of dietary nitrate may be in the range 7.5 g/L-100 g/L for liquids, or 7.5 g/kg-80 g/kg for the powder form. The level of nitrite present in the final form must not exceed 150 mg/L for liquids, or 150 mg/kg for powders.

It is preferred that the composition according to the third aspect of the invention; or, if a significant number of other ingredients are included in a commercial product (see below), a product comprising the composition contains less than 6.5 g/l or less than 6.5 g/kg of nitrate. Preferably the composition or product comprises between about 400 and 4500 mg/l or about 400 and 4500 mg/kg of nitrate. In one embodiment the composition or product comprises about 1.666 g/l or 1.666 g/kg nitrate.

A number of precursors of endogenous nitric oxide may be used according to the invention. Such precursors may be converted within in the body to form nitrates. Examples include citrulline, glutamine and arginine. A most preferred precursor for use according to the invention is citrulline.

It is preferred that the composition according to the third aspect of the invention also comprises folic acid, or metabolites thereof which act as cofactors in the endogenous nitric oxide pathway, as a third component (c). Folic acid is a cofactor that maintains endogenous nitric oxide production by endothelial cells. The inventor has found that the combined effects of a nitrate supplement and folic acid in an experiment (see the Examples) simulating intense exercise was to surprisingly improve the suppression of both platelet activation and the release of inflammatory microparticles. Furthermore compositions of the third aspect of the invention caused an even greater reduction of IL-6 generation in activated endothelial cells, than when water-soluble tomato extract was used alone.

Examples of metabolites of folic acid which may be used according to the invention include 5-methoxytetahydrofolate or tetrahydrofolate.

Sources of folic acid or its metabolites which act as cofactors in the endogenous nitric oxide pathway, suitable for use in the preparation are typically pharmaceutical grade commercial preparations, for example Folic Acid BP/EP, 96% purity, supplied by DSMK.

According to a fourth aspect of the invention there is provided a composition according to the third aspect of the invention for use in treating or preventing exercise-induced systemic inflammation in a subject.

According to a fifth aspect of the invention there is provided a composition according to the third aspect of the invention for use in promoting recovery from exercise in a subject.

The composition according to the third aspect of the invention represents a preferred composition that may be used as discussed in relation to the first and second aspects of the invention and as discussed below.

Pharmaceutical and Nutraceutical Formulations

The fruit extracts used according to the first or second aspects of the invention or compositions of the third aspect of the invention can be prepared without any additional components (e.g. See Example 1 or 2) although in preferred embodiments the extracts and compositions are formulated with other agents, as discussed below and in Example 5, to improve their commercial properties (e.g. to improve delivery, shelf-life, taste and the like).

The fruit extracts and compositions of the invention may be formulated for oral administration. As such, they can be formulated as gels, solutions, suspensions, syrups, tablets, capsules, lozenges and snack bars, beverages, inserts and patches by way of example. Such formulations can be prepared in accordance with methods well known to the art. For example, the extract or composition may be formed into a syrup or other solution for administration orally, for example as a health drink. One or more excipients selected from sugars, vitamins, flavouring agents, colouring agents, preservatives and thickeners may be included in such syrups or solutions. Tonicity adjusting agents such as sodium chloride, or sugars, can be added to provide a solution of a particular osmotic strength, for example an isotonic solution. One or more pH-adjusting agents, such as buffering agents can also be used to adjust the pH to a particular value, and preferably maintain it at that value. Examples of buffering agents include sodium citrate/citric acid buffers and phosphate buffers.

Alternatively, the extract or composition may be dried (e.g. by spray drying or freeze drying) and the dried product formulated in a solid or semi solid dosage form, for example as a tablet, lozenge, capsule, powder, granulate or gel.

Compositions containing the extracts or compositions of the third aspect of the invention may be prepared by adsorbing on to a solid support; for example a support composed of a sugar such as sucrose, lactose, glucose, fructose, mannose or a sugar alcohol such as xylitol, sorbitol or mannitol; or a cellulose derivative. Other particularly useful adsorbents include starch-based adsorbents such as cereal flours for example wheat flour and corn flour.

For tablet formation, the extract or composition may be typically mixed with a diluent such as a sugar, e.g. sucrose and lactose, and sugar alcohols such as xylitol, sorbitol and mannitol; or modified cellulose or cellulose derivative such as powdered cellulose or microcrystalline cellulose or carboxymethyl cellulose. The tablets will also typically contain one or more excipients selected from granulating agents, binders, lubricants and disintegrating agents. Examples of disintegrants include starch and starch derivatives, and other swellable polymers, for example crosslinked polymeric disintegrants such as cross-linked carboxymethylcellulose, crosslinked polyvinylpyrrolidone and starch glycolates. Examples of lubricants include stearates such as magnesium stearate and stearic acid. Examples of binders and granulating agents include polyvinylpyrrolidone. Where the diluent is not naturally very sweet, a sweetener can be added, for example ammonium glycyrrhizinate or an artificial sweetener such as aspartame, or sodium saccharinate.

The extracts or compositions can also be formulated as powders, granules gels, or semisolids for incorporation into capsules. When used in the form of powders, the extracts can be formulated together with any one or more of the excipients defined above in relation to tablets, or can be presented in an undiluted form. For presentation in the form of a gel or semisolid, the dried extracts or compositions can be dissolved or suspended in a viscous liquid or semisolid vehicle such as a polyethylene glycol, or a liquid carrier such as a glycol, e.g. propylene glycol, or glycerol or a vegetable or fish oil, for example an oil selected from olive oil, sunflower oil, safflower oil, evening primrose oil, soya oil, cod liver oil, herring oil, etc. These can then be filled into capsules of either the hard gelatine or soft gelatine type or made from hard or soft gelatine equivalents, soft gelatine or gelatine-equivalent capsules being preferred for viscous liquid or semisolid fillings. In one preferred embodiment, an extract or composition according to the invention is provided in powder form optionally together with a preferred solid (e.g. powdered) excipient for incorporation into capsules, for example a hard gelatine capsule.

A solid or semisolid dosage form of the present invention can contain up to about 1000 mg of the formulation, for example up to about 800 mg.

The extracts of the invention or compositions according to the third aspect of the invention can be presented in the form of unit dosage forms containing a defined concentration of compounds with activity for inhibiting platelet aggregation. Such unit dosage forms can be selected so as to achieve a desired level of biological activity. For example, a unit dosage form can contain an amount of up to 1000 mg (dry weight) of a fruit extract or composition according to the invention, more typically up to 800 mg, for example 50 mg to 800 mg, e.g. 100 mg to 500 mg. Particular amounts of the extract or composition that may be included in a unit dosage form may be selected from 50 mg, 100 mg, 150 mg, 200 mg, 250 mg, 300 mg, 350 mg, 400 mg, 450 mg, 550 mg, 600 mg, 650 mg, 700 mg, 750 mg and 800 mg.

Dosing Regimens

The quantity of the extract used according to the first aspect of the invention or composition according to the invention that needs to be administered to a subject will depend upon a number of factors. For instance when the subject is a human the amount required will depend upon the type of exercise undertaken or to be undertaken; the duration of the exercise; the level of fitness of the person and also factors such as the age, sex and weight of the subject.

For liquid extracts manufactured according to method 1.1 (see Example 1 below), the recommended daily dose of the fruit extract according to the invention is between 0.5 g and 20 g and more preferably between 2 g and 7 g. A daily dose may be about 3 g. A typical dosage regime for a human may be, for each day that they exercise, be from about 70 mg to 285 mg, preferably about 25 mg to 100 mg per kilogram of body weight For powder extracts manufactured according to method 1.2 (see Example 1 below) the recommended daily dose may be between 10 mg and 500 mg and is more preferably between about 85 mg and about 150 mg. A typical dosage regime for a human may be, for each day that they exercise, be from about 1 mg to 2.25 mg per kilogram body weight.

A preferred composition according to the third aspect of the invention comprises water-soluble tomato extract (e.g. in the amount discussed in the preceding paragraphs) and a source of dietary nitrate which provides between 25 mg and 250 mg nitrate per dose, preferably between 50 mg and 150 mg nitrate per dose and most preferably about 100 mg nitrate per dose. It is most preferred that the nitrate is comprised in a composition containing low nitrite levels. Preferably the composition comprises less than 400 mg of nitrate per dose.

A most preferred composition according to the third aspect of the invention comprises water-soluble tomato extract (e.g. in an amount of about 3 g liquid extract per dose) and a source of dietary nitrate (e.g. about 100 mg nitrate per dose) and folic acid. Folic acid may be included in the range 10 to 500 µg per dose, preferably 50 to 400 µg per dose, more preferably 10 to 300 µg per dose; and most preferably about 200 µg per dose.

It is preferred that a subject receives a dose of the extract (and optionally nitrate and folic acid) before exercise. The extract (and optionally nitrate and folic acid) is preferably consumed orally anytime before exercise. For instance a dose could be taken in the morning or at lunch time if exercise is to be undertaken in the afternoon or evening. Preferably the dose is taken between 0 and 5 hours before exercise and more preferably between 1.5 and 3 hours before exercise.

Thus according to a further aspect of the invention there is provided a dosage form comprising the composition according to the third aspect of the invention comprising between 25 mg and 250 mg of nitrate.

It is preferred that the dosage form comprises about 100 mg of nitrate

The dosage form may comprise between 10 µg and 500 µg of folic acid, preferably 50 to 400 µg per dose, more preferably 10 to 300 µg per dose; and most preferably about 200 µg per dose.

The dosage form may comprise water-soluble extract of fruit of the Solanaceae family as described above under the heading dosage regimens.

Preferred Compositions for Human Consumption

The extract or composition can be presented as food supplements or food additives, or can be incorporated into foods, for example functional foods or nutraceuticals.

Gel Products

Aqueous gel products for consumption as a food supplement represent preferred compositions according to the invention. Such gels may be packaged such that the packaging may be torn open and the gel consumed prior to exercise.

The gel products contain a water-soluble extract fruit of the Solanaceae family as defined above. Preferably the gel comprises a source of dietary nitrate or a precursor of endogenous nitric oxide as discussed above and most preferably also comprises folic acid or a derivative thereof. Gel products may additional include one or more of electrolytes, carbohydrate, antioxidants, preservatives, flavouring and sweetener.

Gels should comprise a suitable agent or agents that form an edible gel with the correct consistency to be squeezed from packaging and to be easily consumed A number of suitable gel agents may be used that are known to the art. For instance a gellan gum may be used (e.g. Kelcogel-F). In some embodiments the gel may comprise two gel agents. For instance it may comprise a gellan gum and a xanthan gum.

Preferred gels are defined, and manufactured according to the methods disclosed, in WO 2007/083117 (e.g. as described on pages 19-22 of that specification). It will be appreciated that gels according to the present invention may be isotonic as disclosed in WO 2007/083117 but do not need to be for use according to the invention. For instance the preferred products discussed below and in the Examples are not isotonic. A skilled person will be appreciate that the tonicity of a product can be readily adapted according to need.

A most preferred gel product for use according to the invention may have ingredients in the following ranges:

| Ingredient | Quantity (g/L) |
|---|---|
| Water | 650-890 |
| Kelcogel-F | 1-3 |
| Sodium Citrate | 0.2-0.8 |
| Potassium Sorbate | 0.1-0.5 |
| Sodium Benzoate | 0.1-0.5 |
| Satiaxane CX911 | 1-3 |
| Acesulfame K | 0.2-0.5 |
| Sucralose | 0.05-1.2 |
| Citric Acid | 0.875-1.25 |
| Folic Acid | 0.003 |
| Swiss Chard Juice Concentrate | 55-222 |
| Liquid extract prepared according to 1.1 | 50 |
| Flavouring | 2-7 |

A typical dose for giving to a human athlete will be 10-200 ml of the abovementioned gel, preferably 20-150 ml of gel, more preferably 30-100 ml of gel, more preferably 40-80 ml of gel and most preferably about 60 ml of gel It will be appreciated that many of the above ingredients may be adjusted or substituted by a person skilled in the art of formulating gels for oral consumption. For instance Maltodextrin may be used as an energy source and when this is the case the quantity of water can be reduced by up to 50%

Flavouring may be chosen to prepare a gel of a chosen taste. For instance a preferred gel is banana and mango flavoured. Alternatively blackcurrant, orange or tropical flavours may be used.

Powder Products

Extracts and compositions according to the invention may also be provided in a powder form for reconstitution as a solution. As such they can also contain soluble excipients such as sugars, buffering agents such as citrate and phosphate buffers and may comprise effervescent agents formed from carbonates, e.g. bicarbonates such as sodium or ammonium bicarbonate, and a solid acid, for example citric acid or an acid citrate salt.

Powder extracts prepared according to method 1.2 (below) are preferably used in powder products.

Powder mixes may be used to fill sachets. Preferred sachet mixes will comprise a source of dietary nitrate and most preferred sachet mixes will contain folic acid. A typical sachet powder may comprise:

| Ingredient | Quantity (g/kg) |
|---|---|
| Citric acid | 5-10 |
| Maltodextrin | 650-850 |
| Swiss chard powder | 133-266 |
| Fructose | 20-30 |
| Flavour | 10-20 |
| Powder extract prepared according to 1.2 | 3 |
| Sucralose | 0.5-01 |
| Folic acid | 0.004 |

Example flavour for use in such a sachet mix include lemon and Berry flavours

Such sachet powders may be split into dose units of 10-150 g more preferably about 25-75 g and most preferably are split into 50 g quantities and sealed within sachets. In use the powder may mixed with between 50 and 250 mls of water and consumed before exercise is initiated.

Alternatively powders may be formulated (e.g. by compression of the powder with the optional use of binding agents) to form dispersable tablets (also known as fizz tabs). Typical dispersable tablets may be made to contain ingredients in the following quantities:

| Ingredient | Quantity (g/kg) |
|---|---|
| Electrolyte salts | 0-300 |
| Citric acid | 200-400 |
| Swiss chard powder | 500-800 |
| Powder extract prepared according to 1.2 | 15 |
| Folic acid | 0.017-0.023 |
| Sucralose | 0.5-1.0 |
| Flavour | 10-20 |
| Maltodextrin | 0-200 |

Such tablets may be 1-30 g, preferably 2-20 g and most preferably are formulated as 10 g tablets. In use a 10 g tablet may be dissolved in between 50 and 250 mls of water and consumed before exercise is initiated.

Food Bars

Extracts used according to the invention or compositions according to the third aspect of the invention can also be provided in a powder form for incorporation into snack food bars for example fruit bars, nut bars, and cereal bars. For presentation in the form of snack food bars, the extracts or compositions can be admixed with any one or more ingredients selected from dried fruits such as sun-dried tomatoes, raisins and sultanas, groundnuts or cereals such as oats and wheat.

Preferred food bars may be made to contain ingredients in the following quantities:

| Ingredient | Quantity (g/kg) |
|---|---|
| Mixed fruit juice | 35-80 |
| Swiss chard liquid extract | 83.3-333 |
| Maltodextrin | 100-200 |
| Oats | 50-150 |
| Calcium lactate | 2-5 |
| Fruit flakes/mince | 50-300 |
| Rice/soy crisp | 50-300 |
| Liquid extract prepared according to 1.1 | 75 |
| Flavour | 5-10 |
| Sucralose | 0.5-1.0 |
| Folic acid | 0.005 |

Flavours may, for example, be Apple and blackcurrant, chocolate or blueberry.

It will be appreciated that the size of a food bar can be varied and this will depend on a number of factors (including the amount of water soluble extract, and optionally nitrate and folic acid, included in the bar A typically bar may be 10-200 g, preferably 20-60 g and most preferably about 40 g. Food bar should be consumed before exercise for an optimal effect.

Most referred products comprising extracts according to the invention are defined in Example 5.

The extracts or composition of the invention or formulations thereof can be included in a container, pack or dispenser together with instructions for administration.

Indications of Effectiveness

The ability of compositions comprising extracts of the invention to provide beneficial effects may be assessed with reference to a number of different parameters.

The Examples below provide details of suitable protocols for the assessment of platelet aggregation or primary haemostasis, either of which may be investigated in order to evaluate therapeutic effectiveness. The PFA-100® platelet function analyzer described in the Examples is a relatively new device for the assessment of primary haemostasis, but has been well validated (see, for instance, "The platelet-function analyzer (PFA-100®) for evaluating primary hemostasis" by M. Franchini Hematology, Volume 10, Issue 3 Jun. 2005, pages 177-181).

Measurement of thrombin generating capacity is a standard protocol commonly used for assessment of haematological disorders or efficacy of antithrombotic treatments, and can be carried out either by automated coagulometers or manually.

Circulating cell-derived microparticles are an index of procoagulant capacity and of inflammation, and may be measured most accurately by flow cytometric methods, although other methods also exist.

Measurement of IL-6 is most commonly carried out by ELISA or by automated systems such as Luminex. IL-6 is one of the most widely accepted biomarkers of inflammation.

Evaluation of recovery from exercise is complex, as many systems are involved. However simple measures of wellbeing are reasonably good at monitoring recovery, and some of the most frequently used include: measurement of plasma norepinephrine levels; monitoring muscular strength and power before and after exercise sessions; evaluating muscle soreness after exercise (for example using a validated questionnaire to measure extent of DOMS—Delayed Onset Muscle Soreness); recording sleep disturbances (for example using devices which measure limb movement during sleep); evaluating stress and fatigue (for example using a POMS—Profile Of Mood States—or modified POMS questionnaire, validated for use in athletes); monitoring rates of perceived exertion during exercise (for example using a validated questionnaire system); monitoring heart rates during activity, and monitoring overall mood (for example using a modified POMS questionnaire). These variables have been demonstrated in studies to be reliable indicators of effective recovery. DOMS has also been shown to correlate with circulating IL-6 levels.

Other Aspects of the Invention

According to a further aspect of the present invention there is provided a method of promoting recovery from intense exercise comprising administering to a subject in need of treatment a water-soluble extract of fruit of the Solanaceae family with activity for inhibiting platelet aggregation.

According to another aspect of the present invention there is provided a method of preventing, or reducing the severity of, exercise-induced systemic inflammation comprising administering to a subject in need of treatment a water-soluble extract of fruit of the Solanaceae family with activity for inhibiting platelet aggregation.

According to another aspect of the present invention there is provided use of a water-soluble extract of fruit of the Solanaceae family with activity for inhibiting platelet aggregation for treating or preventing exercise-induced systemic inflammation in a subject.

According to another aspect of the present invention there is provided use of a water-soluble extract of fruit of the Solanaceae family with activity for inhibiting platelet aggregation in the manufacture of a medicament for treating or preventing exercise-induced systemic inflammation in a subject.

According to another aspect of the present invention there is provided use of a water-soluble extract of fruit of the Solanaceae family with activity for inhibiting platelet aggregation for promoting recovery from intense exercise.

According to another aspect of the present invention there is provided use of a water-soluble extract of fruit of the Solanaceae family with activity for inhibiting platelet aggregation in the manufacture of a medicament for promoting recovery from intense exercise.

BRIEF DESCRIPTION OF THE DRAWINGS

The invention will now be illustrated, but not limited, by the following examples, and with reference to the accompanying drawings, in which.

EXAMPLE 1

Figure 2:
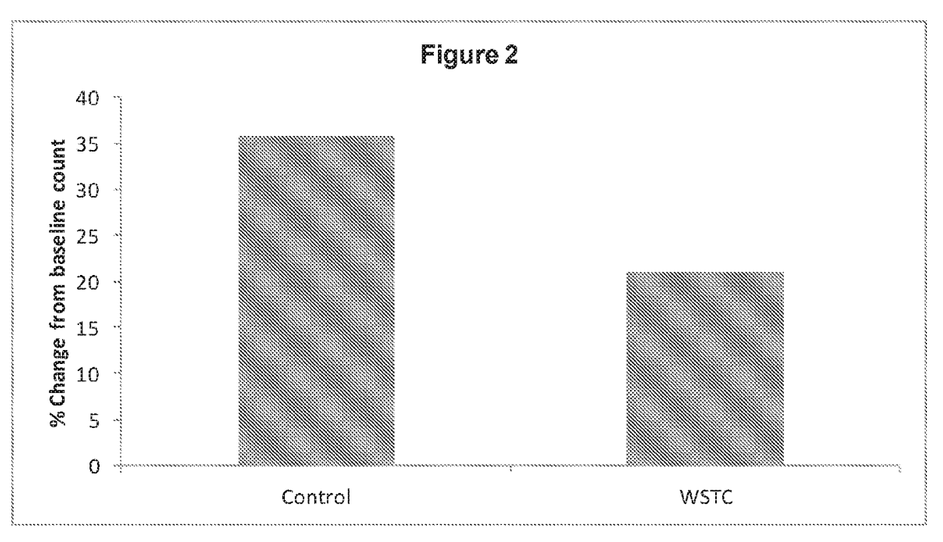
FIG. 2: illustrates the effects of treatment with water-soluble tomato extract (WSTC) on microparticle release from platelets exposed to thrombin and epinephrine as discussed in Example 3.

A water-soluble extract of tomato with activity for inhibiting platelet aggregation was prepared by following the protocols:

1.1 A liquid (syrup) extract which may be used according to the invention, was prepared following the protocols of Example 2 and FIG. 2 of WO 2010/049707.

Figure 4:
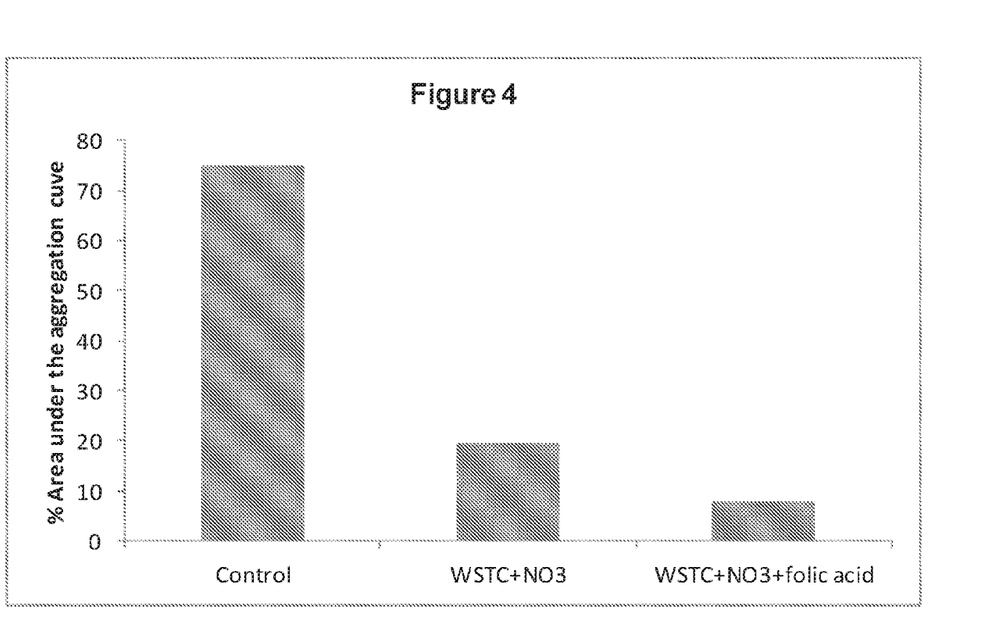
FIG. 4: illustrates the effects of incubating platelet-rich plasma with water-soluble tomato extract (WSTC)+dietary nitrate (NO3); and water-soluble tomato extract (WSTC)+ dietary nitrate+folic acid on platelet aggregation in response to thrombin and epinephrine as discussed in Example 4.

1.2 A powder extract (with low sugar content), which may be used according to the invention, was prepared following the protocols of Example 3 and FIG. 4 of WO 2010/049707.

EXAMPLE 2

Example 2 provides methods of preparing a preferred composition according to the third aspect of the invention, comprising a combination of water-soluble tomato extract, a source of dietary nitrate, and a source of folic acid.

2.1 The water-soluble tomato extract should be sourced and prepared as outlined in Example 1. A solution of this extract at a concentration of 430 µg/ml was prepared by either diluting the extract described in Example 1.1, or by dissolution of the powdered extract described in Example 1.2, in deionised water. The resulting solutions at 430 µg/ml were buffered to pH 7.4 for use in experimental protocols in which they were further diluted tenfold to give a final working concentration of 43 µg/ml. This concentration represents the maximum calculated circulating plasma concentration of antiplatelet compounds within the extract approximately 3 hours after ingestion of a most preferred unit dose (3 g liquid extract (1.1), 150 mg powder extract (1.2).

2.2 An extract rich in dietary nitrate was sourced from Diana Naturals, France. This comprised a water-soluble Swiss chard extract of approximately 60 Brix, which contained inorganic nitrate at a level of approximately 20 g/L and inorganic nitrite at a level of less than 150 mg/L. A solution of this extract at a concentration of 186 mg/ml nitrate was produced by dilution of the original extract in deionised water. The resulting solution was buffered to pH 7.4 for use in experimental protocols in which it was further diluted tenfold to give a final working concentration of 18.6 mg/ml. This concentration of Swiss chard extract corresponds to a final working concentration of 372 ng/ml nitrate. Based on published data in which dietary nitrate has been consumed in the form of vegetable extracts, this concentration of 372 ng/ml nitrate in plasma could be obtained 3 hours after consuming a 100 mg dose of dietary nitrate (Cermak N et al, Int J Sport Nutr Exerc Metab 2012, 22, 64-71).

2.3 The source of folic acid was Folic acid EP/BP from supplier DMSK. This material is water-insoluble and so a solution of this material at a concentration of 50 ng/ml was produced by dissolution in dilute acid. The resulting solution, once prepared, was successfully buffered to pH 7.4 without precipitation of material, and was used in experimental protocols in which it was further diluted tenfold to give a final working concentration of 5 ng/ml. This corresponds to a typical plasma folate concentration 3 hours after supplementation with multivitamin / mineral supplements supplying the UK RDA of 200 µg folic acid (Navarro M et al, JACN, 2003, 22, 124-132).

2.4 Using components sourced and prepared as described above, a mixture was prepared by mixing in equal quantities the prepared extract solution described in 2.1, and the prepared dietary nitrate solution described in 2.2. This mixture, when diluted tenfold in experimental protocols, gives final concentrations of 43 mg/ml of extract and 372 ng/ml of dietary nitrate. These quantities represent approximate concentrations of each component expected to circulate in plasma 3 hours after ingestion of 3 g syrup extract (1.1) and 100 mg dietary nitrate from 5 g Swiss chard extract.

2.5 Using components sourced and prepared as described above, a mixture was prepared by mixing in equal quantities the prepared extract solution described in 2.1, the prepared dietary nitrate solution described in 2.2 and the prepared folic acid solution described in 2.3. This mixture, when diluted tenfold in experimental protocols, gives final concentrations of 43 mg/ml of extract; 372 ng/ml of dietary nitrate and 5 ng/ml of folic acid. These quantities represent approximate concentrations of each component expected to circulate in plasma 3 hours after ingestion of 3 g WSTC syrup concentrate, 100 mg dietary nitrate from 5 g Swiss chard extract, and 200 µg folic acid. This active ingredient mix represents a preferred composition according to the third aspect of the invention. The mix may be added gel agents and other excipients to a make a final gel product volume of 60 ml.

EXAMPLE 3

The present invention is based upon research that surprisingly established that water-soluble tomato extract modulates three biological systems which are affected by intense exercise, and which represent different aspects of the inflammatory response engendered by intense exercise. These three biological systems are: blood platelets, part of the haemostatic system known to be strongly activated by intense exercise, due to the exercise-induced release of thrombin and ephinephrine into the bloodstream and depletion of circulating nitric oxide; circulating plasma cell-derived microparticles, an index of platelet and leukocyte activation and of inflammation; and endothelial cell cytokine release, in particular the cytokine IL-6, one of the best validated markers of inflammation. It may be considered that intense exercise induces a chain reaction leading to systemic inflammation, which starts with platelet activation and platelet-leukocyte microparticle release, followed by endothelial cell cytokine release as a result of exposure to the activated blood cells and microparticles produced. This systemic inflammation can lead to delays in recovery from exercise, and difficulties in sustaining the high-intensity exercise sessions required for performance improvement.

The inventor examined the efficacy of different amounts of water-soluble tomato extract components in preventing thrombin and epinephrine induced platelet aggregation, procoagulant and proinflammatory microparticle release from platelets and leukocytes, and endothelial cell cytokine release. Levels of thrombin and epinephrine used were consistent with levels measured in blood during high-intensity exercise.

3.1. METHODS 3.1.1 Preparation of a Tomato Extract for Use as a Treatment Solution, and of a Control Solution To prepare solutions of tomato extract suitable for use in experiments examining its biological activities, liquid tomato extract of 62° Brix, prepared as described in Example 1, was diluted to a concentration of 430 μg/ml as described in Example 2.1. Phosphate-buffered saline (PBS, Sigma-Aldrich UK) was prepared as a control solution.

3.1.2 Methods of Assaying Activity for Inhibiting Platelet Aggregation

The experimental protocol described below was devised to compare the extent of inhibition of platelet aggregation triggered by combinations of the thrombin analogue TRAP (thrombin receptor activating peptide) and epinephrine (relevant to an intense exercise load) which was achieved after incubation of platelets with either prepared extracts or with controls.

Phlebotomy and Blood Samples

Blood for in vitro studies was collected from drug-free, healthy human volunteers, both male and female, aged 18-60 years, with normal platelet function. Subjects declared that they had not consumed drugs or supplements known to affect platelet function for a minimum of 10 days before providing a blood sample. Blood was collected after single venepuncture to an antecubital vein through siliconized needles into plastic citrated blood collection tubes (Sarstedt Monovettes, final concentration sodium citrate, 13 mmol/L). All blood was maintained at 37° C. from the time of blood sampling.

Preparation of Platelet-Rich Plasma

Platelet-rich plasma (PRP) was obtained by centrifugation of citrated blood for 15 minutes at 200×g, and was adjusted with platelet-poor plasma to a standard platelet number of $320\pm20\times10^9$/L prior to use. PRP was used for platelet function measurements within two hours.

Platelet Agonists

The following agonists were used for platelet function measurements. TRAP, final concentration 2 nmol/L; epinephrine, final concentration 0.15 μmol/L (both from Sigma-Aldrich, Poole, UK). Agonists were prepared from stock solutions immediately before use by diluting into warmed physiological saline (0.9% NaCl), and mixed to give a combined TRAP/epinephrine agonist. At these concentrations, neither agonist was able to induce a platelet aggregation response individually. However in combination, the potentiating effect of epinephrine on TRAP resulted in a strong platelet response.

Incubation of Treatment Solutions (3.1.1) With PRP

180 μL PRP was incubated with 20 μL prepared treatment or control solutions at 37° C. for 10 minutes, in low-retention epindorrfs.

Measurement of Platelet Aggregation and Inhibition of Aggregation

Figure 1:
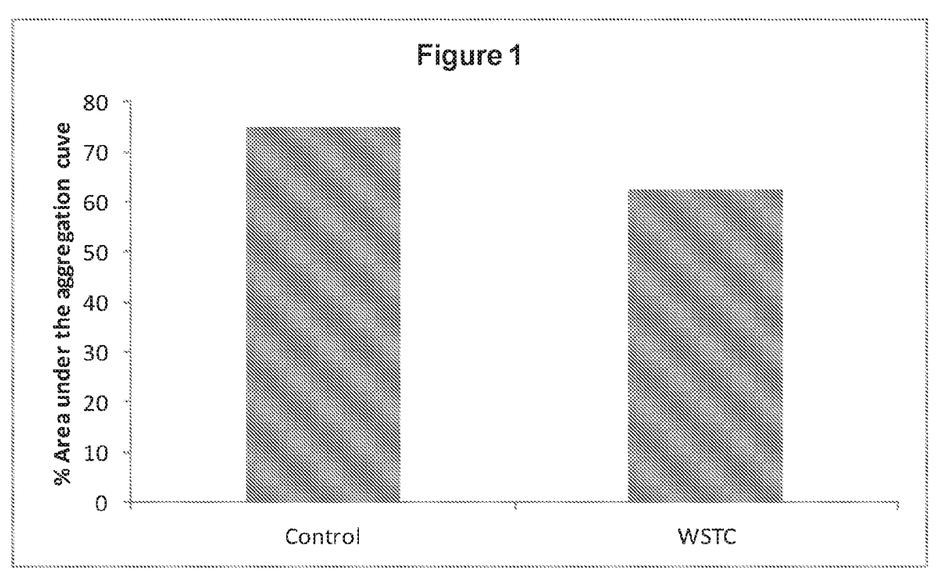
FIG. 1: illustrates the effects of incubating platelet-rich plasma with water-soluble tomato extract (WSTC) on platelet aggregation in response to thrombin and epinephrine as discussed in Example 3.

After incubation with platelet inhibitors, PRP samples were transferred to glass cuvettes and the extent of aggregation induced by the combined TRAP/epinephrine agonist was monitored over 10 minutes on a platelet aggregometer (Aggram, Helena Biosciences, Sunderland, UK). From the aggregation curves generated, the area under the curve was calculated for each PRP sample, and the inhibition of aggregation achieved by the treatment solution was calculated by comparing the area under the curve for these PRP samples with that of the control sample. Results are shown in FIG. 1.

3.1.3 Methods of Assaying Release of Cell-Derived Microparticles

The experimental protocol described below was devised to compare the number of platelet-derived microparticles released from intact platelets after exposure to combinations of thrombin and epinephrine (relevant to an intense exercise load), in the presence of either prepared extracts or controls.

Phlebotomy and Blood Samples

Blood for in vitro studies was collected from drug-free, healthy human volunteers, both male and female, aged 18-60 years, with normal platelet function, as described in 3.1.2 above.

Preparation of Platelet-Poor Plasma

Within 10 minutes of collection, citrated whole blood was centrifuged at 2000 g for 20 min at room temperature to isolate platelet-poor plasma (PPP).

Preparation of Agonists

Agonists used to stimulate activation of platelets in a manner designed to simulate intense exercise were again combinations of thrombin and ephinephrine, and these were prepared as described in 3.1.2 above.

Preparation of Extracts and Control Solutions

Treatment and control solutions for incubation with the prepared PPP were prepared as described in 3.1.2 above.

Incubation of Treatment Solutions With PPP

180 μL PPP was incubated with 20 μL prepared treatment or control solutions at 37° C. for 10 minutes, in low-retention epindorrfs.

Measurement of Microparticles Before and After Treatment With Thrombin-Epinephrine Platelet-derived microparticles were detected by flow cytometry, which allows quantification of labelled particles in solution/suspension. The PPP samples pre-treated with treatment or control solutions were activated by addition of either TRAP/epinephrine combined agonist, or PBS, and were left to stand for 10 minutes. The activated samples were then incubated with different fluorescence-labelled antibodies. Anti-CD61-PerCP monoclonal antibody (BD Bioscience, San Jose, Calif., USA) was used to detect platelet-derived microparticles. Anti-CD45-PE (BD Pharmingen, BD Bioscience) monoclonal antibodies were used to label LMP. PE- and PerCP conjugated isotype controls (IgG1, BD Bioscience) were used to define the background noise. 25 μL activated PPP was incubated with 5 μL each antibody in the dark for 20 min at room temperature, then 470 μL cold (4° C.) FACSFlow (FACSFlow Sheath Fluid, BD Bioscience) was added.

These samples were run through a FACSCalibur flow cytometer, and antibody-labelled particles were counted within the microparticle gate (at <1 μ, determined by 1 μ beads). Data were acquired and analysed with CellQuest software (version 2: BD Biosciences) after counting for 100 seconds on high flow rate. Microparticle concentration in each sample was calculated by the read volume, which was estimated by the reading time multiplied by the sample flow rate. Results are expressed in number of microparticles per µl PPP, and shown in FIG. 1.

3.1.4 Methods of Measuring Release of IL-6 From Endothelial Cells Incubated With Tomato Extract Treatment and Control Solutions Preparation of Treatment Extracts and Control Extracts Treatment and control solutions for incubation with cell suspensions were prepared as described in 3.1.2 above.

Preparation of Activated Platelet-Leukocyte Suspensions and Inactivated Control Suspensions, in the Presence of Treatment and Control Extracts 450 µl citrated whole blood was aliquoted into 2 12 ml low-retention tubes. 4.5 ml diluted lyse reagent (Haemolyse, Sigma-Aldrich UK), diluted tenfold from original stock solution, was added to each, the tubes capped and mixed well, and left to stand at room temperature for 10 minutes. The haemolysed samples were then centrifuged at 400 g for 10 minutes. 4.5 ml of the supernatant was removed and discarded. 250 µl Hepes-Mg buffer was added to the pellets, mixed and transferred to an eppendorff. The tubes were washed with a further 250 µl Hepes-Mg buffer and the washings transferred to give a volume of approximately 1 ml. The suspensions were mixed and then centrifuged as before. 900 µl of the supernatant was removed and discarded. To the remaining 100 µl in each tube, 250 µl Hepes-Mg buffer was added and the suspensions were thoroughly mixed. The cells in suspension were counted using a Sysmex Haematology Analyser (Sysmex UK), and the final suspension volume was adjusted to give a leukocyte cell count of $3.3-3.4 \times 10^3$/µl.

To one suspension, TRAP/epinephrine agonist was added in an amount such that a tenfold dilution of the stock solution was achieved, and an activated cell suspension resulted. To the second suspension, PBS and 10 µl prostaglandin E2 solution was added, in order to keep the cells in an inactivated state.

Preparation of Endothelial Cell Cultures

Human umbilical vein endothelial cells (HUVEC) (Lonza Switzerland) were cultured in T75 cm flasks in EBM-2 medium (Lonza, Switzerland) with the addition of the EGM-2 bullet-kit supplements, consisting of growth factors and antibiotics, specific for that medium. The cells were maintained at 37° C. in the presence of 5% $CO_2$. This medium was changed every 2 days and cells always were subcultured prior to confluence.

At approximately 75% confluence cells were subcultured into 6-well plates. First the medium of the T75 flask was discarded and the remaining cell monolayer washed with ~2 ml of d-PBS (Lonza, Switzerland) three times. Just after, 2 ml of trypsin (Lonza, Switzerland) were added in order to separate the cell layer from the flask wall. The flask (T75) was then inspected under the microscope to ensure the removal of all of the cells from the bottom of the flask. After 2 min, ~2 ml of Foetal Bovine Serum (FBS) was added in order to inhibit digestion of cells by trypsin. After, the remaining volume was measured and the rest of medium required to fill the 6-well plates (2 ml each well) was added. The plates were maintained at 37° C. until cells were 100% confluent for 1-2 days before undergoing further treatment.

Treatment of Endothelial Cells

Confluent HUVECs were cultured in EMB-2 with treatment or control solutions prepared as described, for 24 h. Treatment and control solutions were diluted in cell culture media prior to incubation and added in an amount sufficient to achieve a tenfold dilution of the prepared stock solutions. After 24 h of treatment, the media was collected into three equal aliquots per well, snap frozen in liquid nitrogen and stored at −80° C. Fresh media was added to the cells for further treatments. The cells were incubated for a further 24 h with 3 ng/ml TNF-α, or 1 ml of the activated platelet-leukocyte suspension described above, maintaining one of the wells free of stimulants in order to have a control.

Method of Assaying Released IL-6

IL-6 was detected by ELISA, as described by the manufacturer's instructions (Biosource, UK). In brief, 1:2 diluted cell culture supernatant (100 µl) was incubated for 1 hr, wells were then washed 4-5 times with wash buffer and filled with 100 µl of anti-IL-6 conjugate and 50 µl of solution A. After 1 hr incubation at room temperature, wells were washed again and filled with 200 µl of chromogen to each well and incubate for 15 min. The reaction was terminated by adding 100 µl of stop solution. Absorbance values were read at 450 nm. Standard curves were obtained by assaying different IL-6 standards (with concentrations from 16 to 1690 pg/ml) provided in the kits.

Figure 3:
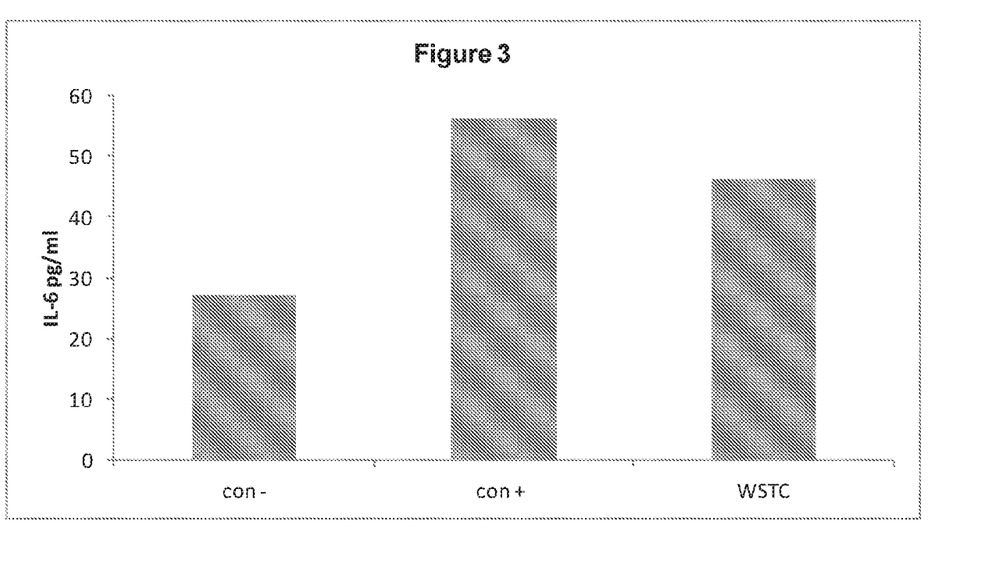
FIG. 3: illustrates the effects of treatment with water-soluble tomato extract (WSTC) on endothelial cell release of IL-6 after exposure to platelets and microparticles activated by thrombin and epinephrine as discussed in Example 3. 'Con−' represents control HUVEC cells not treated with activated platelet-leukocyte suspension. 'Con+' represents HUVEC cells treated with platelet-leukocyte suspension and using saline as treatment. WSTC represents HUVEC cells incubated with activated platelet-leukocyte suspension and using WSTC as treatment.

Results of experiment 3.1.4 are shown in FIG. 3.

3.2 Results

The results of the experiments described are shown in graphical format in FIGS. 1, 2 and 3.

3.3 Conclusions

The experiments undertaken show that water-soluble extract of fruit of the Solanaceae family is capable of suppressing the platelet activation contingent upon intense exercise, characterised by an increase in thrombin and epinephrine-mediated activation, and which is largely unaffected by known antiplatelet drugs. Further, this primary action of the extract results in suppression of platelet microparticle release, a result of platelet activation. Platelet microparticles make up approximately 70% of the circulating cell microparticle population, and are acknowledged as a significant inflammatory signalling system operating throughout the body. They are also highly procoagulant, and capable of exacerbating thrombin release and maintaining a procoagulant and proinflammatory state for many hours after cessation of exercise. The effects of platelet and leukocyte microparticles, generated by thrombin and epinephrine, on endothelial cells was demonstrated to be an increase in IL-6 release from the endothelial cells. Pretreatment of the endothelial cells with solution of extract according to the invention in physiologically relevant amounts was shown to suppress this IL-6 release, resulting in lowered inflammatory status of the endothelium. Suppression of circulating IL-6 has been shown in other studies to affect recovery times and delayed onset muscle soreness. Therefore pretreatment with water-soluble extract of fruit of the Solanaceae family before vigorous exercise helps to promote recovery after exercise.

EXAMPLE 4

The inventor also examined the efficacy of preferred compositions according to the third aspect of the invention, described in Example 2, in preventing activation of the biological systems examined in Example 3.

4.1. METHODS 4.1.1 Preparation of Combinations of Water-Soluble Tomato Extract With Sources of Dietary Nitrate and Folic Acid for Use as Treatment Solutions, and of a Control Solution For use in experiments examining the biological activities of water-soluble extract of fruit of the Solanaceae family combined with dietary nitrates and folic acid, the preferred formulations described in Examples 2.4 and 2.5 were used. PBS was prepared as a control solution.

4.1.2 Methods of Assaying Activity for Inhibiting Platelet Aggregation

The experimental protocol described in 3.1.2 was followed in exact detail, with the exception that treatment solutions as described in 4.1 were used. Results are shown in FIG. 4.

4.1.3 Methods of Assaying Release of Cell-Derived Microparticles

The experimental protocol described in 3.1.3 was followed in exact detail, with the exception that treatment solutions as described in 4.1 were used. Results are shown in FIG. 5.

4.1.4 Methods of Measuring Release of IL-6 From Endothelial Cells Incubated With Tomato Extract Treatment and Control Solutions The experimental protocol described in 3.1.3 was followed in exact detail, with the exception that treatment solutions as described in 4.1 were used. Results are shown in FIG. 6.

4.2 Results

Figure 5:
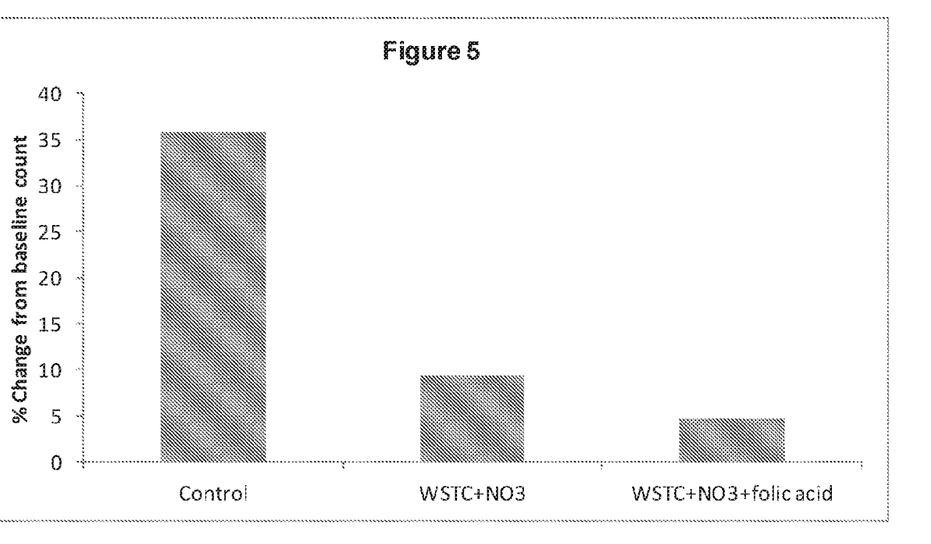
FIG. 5: illustrates the effects of treatment with water-soluble tomato extract (WSTC)+dietary nitrate (NO3); and water-soluble tomato extract+dietary nitrate+folic acid on microparticle release from platelets exposed to thrombin and epinephrine as discussed in Example 4.
Figure 6:
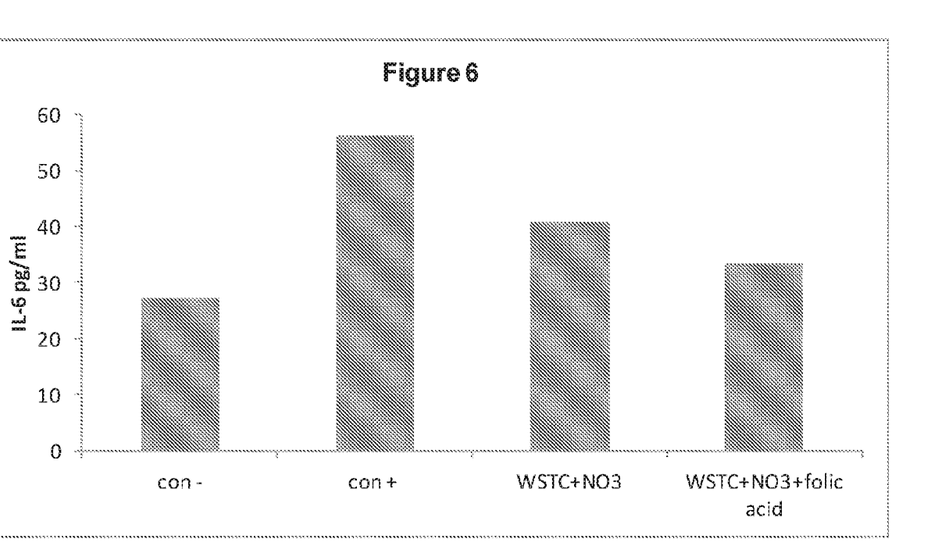
FIG. 6: illustrates the effects of treatment with water-soluble tomato extract (WSTC)+dietary nitrate (NO3); and water-soluble tomato extract+dietary nitrate+folic acid on endothelial cell release of IL-6 after exposure to platelets and microparticles activated by thrombin and epinephrine as discussed in Example 4. 'Con −' represents control HUVEC cells not treated with activated platelet-leukocyte suspension. 'Con+' represents HUVEC cells treated with platelet-leukocyte suspension and using saline as treatment. WSTC+ NO3 and WSTC+NO3+folic acid represents HUVEC cells incubated with activated platelet-leukocyte suspension and using WSTC+NO3 or WSTC+NO3+folic acid as treatment, respectively.

The results of the experiments described are shown in graphical format in FIGS. 4, 5 and 6.

4.3 Conclusions

Through the experiments undertaken in Example 4, the inventor was able to show a significant improvement in bioactivity for combinations of water-soluble extract of fruit of the Solanaceae family with dietary nitrate extracts, with and without the addition of folic acid. The combination of the extract with both dietary nitrate and folic acid was the most efficacious examined, in terms of effects on platelet aggregation, platelet microparticle generation, and endothelial cell IL-6 release after exposure to activated platelets, leukocytes and increased levels of associated microparticles. For inhibition of exercise induced platelet aggregation and microparticle release, this preferred combination was more than twice as efficacious as WSTC used alone; while for inhibition of IL-6 generation from endothelial cells after exposure to activated platelets and leukocytes, it was almost three times as efficacious.

These results show, while water-soluble extract of fruit of the Solanaceae family alone surprisingly and beneficially affects systemic inflammation induced by exercise, that its efficacy can be materially and inventively increased further by combining it with dietary nitrate and folic acid.

EXAMPLE 5

In view of the knowledge gained with regards to combinations of water-soluble tomato extract and sources of nitric oxide which showed best overall efficacy, the inventor proceeded to develop compositions which may be used to appropriately deliver these combinations in advance of and during periods of intense exercise.

5.1 Gels

A gel product was manufactured according to the methods disclosed in WO 2007/083117 (as described on pages 19-22 of that specification) with the exception that the gel product (see below) was not designed to be isotonic.

A most preferred gel product for use according to the invention may comprise:

| Ingredient | Quantity (g/L) |
|---|---|
| Water | 848 |
| Kelcogel-F | 2.4 |
| Sodium Citrate | 0.4 |
| Potassium Sorbate | 0.2 |
| Sodium Benzoate | 0.2 |
| Satiaxane CX911 | 2.4 |
| Acesulfame K | 0.3 |
| Sucralose | 0.08 |
| Citric Acid | 1 |
| Folic Acid | 0.003 |
| Swiss Chard Juice Concentrate | 90 |
| Liquid extract prepared according to 1.1 | 50 |
| Flavouring* | 5.5 |

*Flavouring may be banana and mango. Alternatively blackcurrent, orange or tropical flavours may be used.

Gels may be packaged into laminated foil sachets to ensure shelf life, using for example a gel packaging machine such as made by Universal Pack. Typical gel sizes range from about 40 ml to about 100 ml (e.g. they may be 60 mls).

5.2 Sachet Powder

Powder mixes may be made to contain ingredients in the following quantities:

| Ingredient | Quantity (g/kg) |
|---|---|
| Citric acid | 7 |
| Maltodextrin | 755 |
| Swiss chard powder | 200 |
| Fructose | 22 |
| Lemon flavour | 12 |
| Powder extract prepared according to 1.2 | 3 |
| Sucralose | 0.6 |
| Folic acid | 0.004 |

Such powder mixes can be made by conventional dry-blending techniques, for example using a ribbon blender or similar, under suitable factory conditions controlling dust and humidity. Agents may be added to ensure free-flow of the resultant powder, e.g. anticaking agents. Packaging into suitable containers such as tubs or sachets should be done under conditions of strict dust control and controlled humidity.

The powders may be split into 50 g dose units and sealed within sachets. In use the powder is mixed with between 50 and 250 mls of water and consumed before exercise is initiated.

5.3 Fizz Tab

Dispersable tablets (also known as fix tabs) may be made to contain ingredients in the following quantities:

| Ingredient | Quantity (g/kg) |
|---|---|
| Electrolyte salts | 2.5 |
| Citric acid | 300 |
| Swiss chard powder | 670 |
| Powder extract prepared according to 1.2 | 15 |
| Folic acid | 0.02 |
| Sucralose | 0.8 |
| Flavour | 10 |
| Maltodextrin | 2.5 |

Fizz tab formulations can also be made by conventional dry-blending techniques, for example using a ribbon blender or similar, where the whole process is carried out under controlled atmospheric conditions with relative humidity less than 10. Compression of tablets from the blended dry ingredients may be carried out by a range of tablet pressers capable of exerting pressures of the order of 5-10 tonnes, depending on desired tablet size. Packaging into individual sachets or multitubes must be carried out under conditions of controlled humidity and individual packets should contain sufficient dessicant material to ensure shelf life and tablet stability Such tablets are made up as 10 g tablets. In use the tablet is dissolved in between 50 and 250 mls of water and consumed before exercise is initiated.

5.4 Food Bars

Food bars may be made to contain ingredients in the following quantities:

| Ingredient | Quantity (g/kg) |
|---|---|
| Mixed fruit juice | 50 |
| Swiss chard liquid extract | 125 |
| Maltodextrin | 140 |
| Oats | 60 |
| Calcium lactate | 3 |
| Fruit flakes/mince | 290 |
| Rice/soy crisp | 250 |
| Liquid extract prepared according to 1.1 | 75 |
| Flavour* | 7 |
| Sucralose | 0.8 |
| Folic acid | 0.005 |

*Flavours may, for example, be Apple and blackcurrant, chocolate or blueberry

An appropriate process for making a food bar involves heating the fruit juices to approximately 100° C. to remove some moisture, followed by mixing in dry ingredients and pasteurising. The mixer contents may then be emptied onto trays or conveyors, and rolled to a suitable height, typically 10-15 mm, using an industrial roller. Fans may be employed to cool the mixture during this process, after which the bars may be cut to the required size using mechanical guillotines. Bars may be packaged individually by flowrap into aluminium foil to retain freshness.

40 g bars are a suitable dose unit and should be consumed before exercise.

EXAMPLE 6

The inventor also examined the efficacy of a preferred composition according to the invention, manufactured in the form of a gel as described in Example 5, in preventing platelet and coagulation system activation and the increases in plasma IL-6 levels associated with a set period of exercise conducted at 70% $VO_2$ max.

6.1. METHODS 6.1.1 Subjects

Three healthy male subjects, aged 18-55, whose $VO_2$ max had previously been determined, were recruited.

6.1.2 Supplements

Two test gels were prepared, as described in Example 5. Gels were packaged in foil packs of 60 ml volume. The treatment gel (FF) contained 3 g of water-soluble tomato extract (WSTC) 5.4 g Swiss Chard Juice Concentrate equivalent to approximately 100 mg dietary nitrate, and approximately 200 µg folic acid. The placebo gel contained 3 g glucose syrup in place of this mixture.

6.1.3 Exercise Protocol

All subjects undertook two exercise protocols, separated by at least 72 hours. Subjects presented at the research facility in a fasted condition, and a baseline blood sample was taken using trisodium citrate as anticoagulant. Subjects were given a set breakfast, at which a single test gel was consumed, randomly assigned to be treatment (FF) or placebo (P). After 90 minutes, a pre-test blood sample was taken. Subjects then undertook a 20 minute treadmill run at 70% $VO_{2max}$. On completion of the treadmill run, subjects ran at 90% $VO_{2max}$ until volitional exhaustion. A post-exercise blood sample was taken, after which subjects were given a snack lunch and were free to depart. Subjects returned to the facility 72 hours later and repeated the test day, incorporating the remaining test gel.

6.1.5 Sample Analysis

Within 20 minutes of collection, citrated whole blood was centrifuged at 2000 g for 20 minutes at room temperature to isolate platelet-poor plasma. Aliquots were frozen for determination of thrombin generating capacity, an index of the activity of the coagulation system, which was measured using a fluorescence-based assay (Thrombin Generation Assay, Technoclone, UK), and for measurement of plasma IL6 (by ELISA from Biosource, UK as described in 3.1.4). The remaining platelet-poor plasma was used immediately for measurement of circulating microparticles, an index of the activity of circulating platelets (as described in 3.1.3).

6.2 Results

Figure 7:
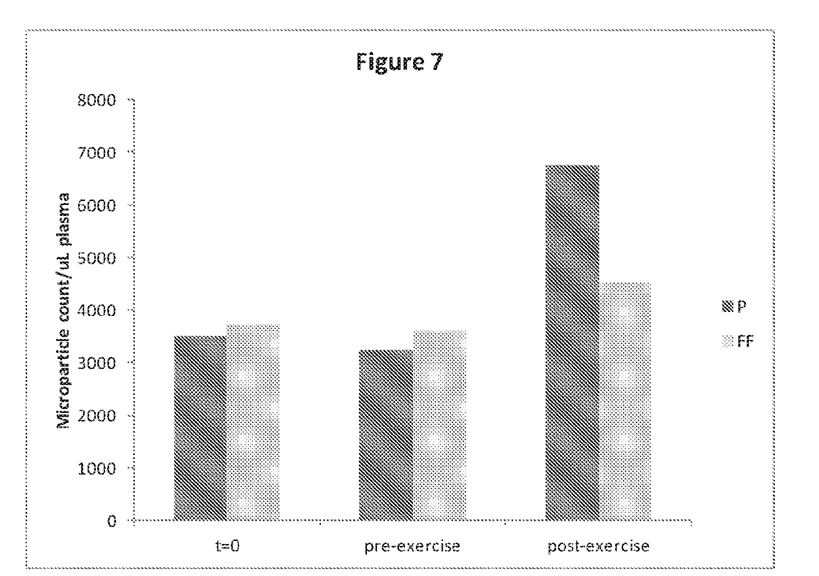
FIG. 7: Platelet derived microparticle count at baseline (before supplementation), pre-exercise (after supplementation) and post-exercise in healthy subjects (n=3). P=placebo supplementation. FF=preferred combination of WSTC, dietary nitrate and folic acid as discussed in Example 6.
Figure 8:
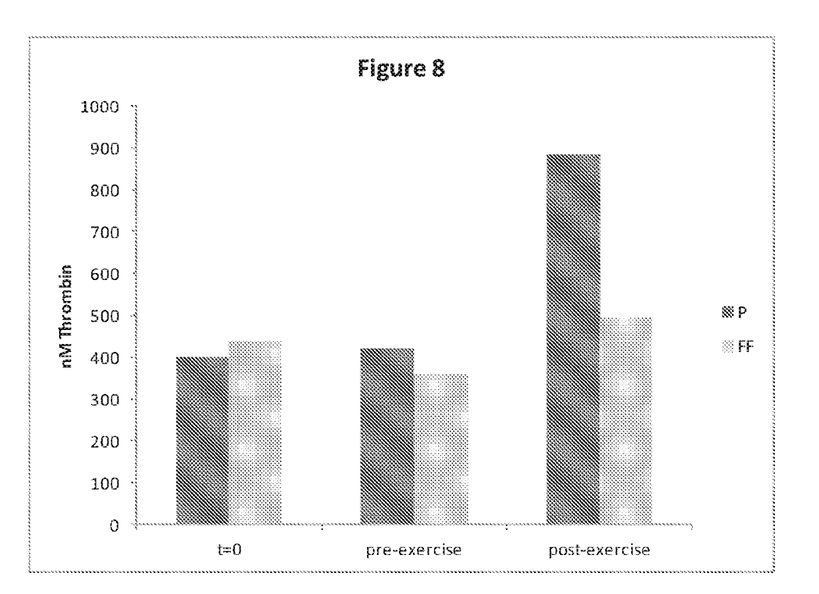
FIG. 8: Plasma thrombin generating capacity (nM) at baseline (before supplementation), pre-exercise (after supplementation) and post-exercise in healthy subjects (n=3). P=placebo supplementation. FF=preferred combination of WSTC, dietary nitrate and folic acid as discussed in Example 6.
Figure 9:
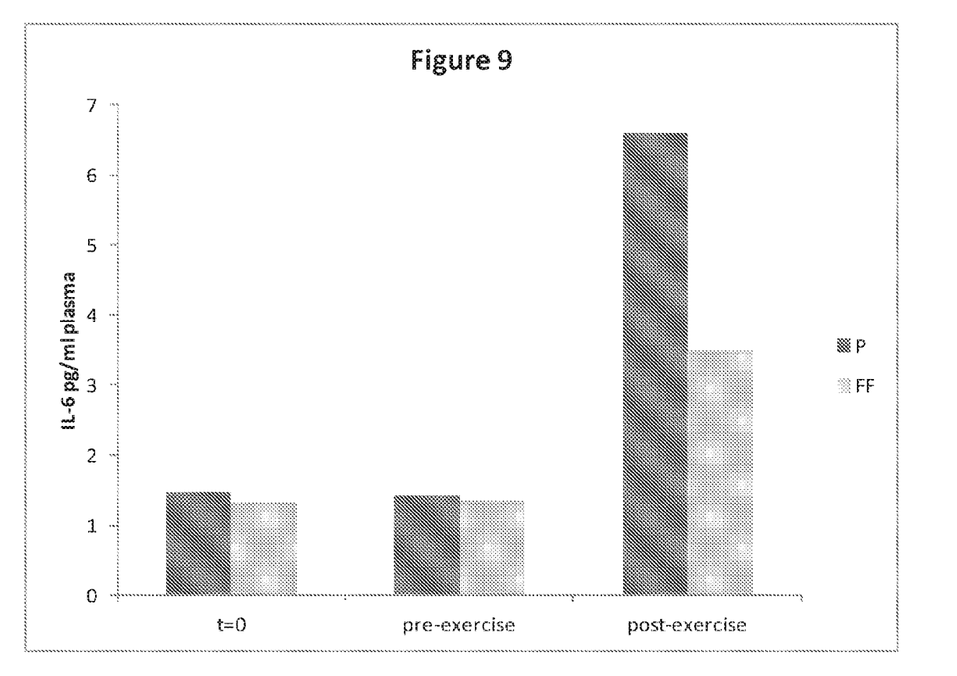
FIG. 9: Circulating plasma IL-6 concentration (pg/ml) at baseline (before supplementation), pre-exercise (after supplementation) and post-exercise in healthy subjects (n=3). P=placebo supplementation. FF=preferred combination of WSTC, dietary nitrate and folic acid as discussed in Example 6.

The results of the experiments described are shown in graphical format in FIGS. 7, 8 and 9.

6.3 Conclusions

Through the experiment undertaken in Example 6, the inventor was able to show the efficacy of a combination of WSTC, dietary nitrate and folic acid in reducing the activation of platelets and the coagulation system after 20 minutes of moderate to strenuous exercise, compared to placebo. This reduction in haemostatic activation was accompanied by a reduction in circulating plasma IL6 for the FF treatment, compared to placebo.

Platelet microparticle count was used in this experiment as an index of platelet activation. Baseline microparticle count did not change significantly after consumption of the test gels in either the FF or the P test groups. However post-exercise, the number of circulating platelet microparticles increased 1.9-fold in the placebo group, compared to 1.2-fold in the FF group. That is, the FF treatment appeared to reduce the exercise-induced release of platelet microparticles by around 70%, compared to placebo.

Thrombin generation capacity was not altered from baseline after consumption of the P gel, but was reduced by 19% after consumption of the FF gel (pre-exercise). This is likely due to an acute inhibition of platelet function. Post-exercise, thrombin generation capacity increased by 2.2-fold in the P test group. In the FF test group, thrombin generation capacity following exercise was increased by 1.4-fold compared to the pre-exercise levels; this represents an increase from baseline thrombin generating capacity of 1.1-fold. Thus, whereas exercising while taking placebo treatment was accompanied by over 120% increase from baseline thrombin generating capacity, FF treatment effectively restricted this increase to 13% from baseline.

Baseline IL6 levels were not affected by consumption of either gel (pre-exercise). Levels of circulating IL6 increased by 4.5-fold in the placebo group post-exercise, while in the FF group, levels increased 2.6-fold. Thus exercising after the FF treatment resulted in only 42% of the increase in plasma IL6 observed after exercising after the placebo treatment.

In summary, consuming the FF treatment significantly reduced exercise-associated release of platelet microparticles, and the related increase in plasma thrombin generating capacity, as well as the levels of systemic IL6 induced by exercise. These results show, that the preferred combination of WSTC, dietary nitrate and folic acid can beneficially affect systemic inflammation induced by exercise and therefore demonstrates that compositions according to the invention will promote recovery from exercise.

The invention claimed is:

1. A method of treating a human suffering from post exercise muscle soreness consisting essentially of:
   administering a composition consisting essentially of a therapeutically effective amount of a water soluble tomato extract and a therapeutically effective amount of a dietary nitrate to the human in need thereof;
   wherein the lycopene content of the water soluble tomato extract is less than 0.5% by dry weight of the water soluble tomato extract, and the water insoluble particulate material is less than 0.1% by dry weight of the water soluble tomato extract, and
   wherein the water soluble tomato extract is made by a process consisting essentially of:
   preparing a start mix of homogenized tomato, wherein the pH of the start mix does not exceed pH 5.5, the holding temperature of the start mix does not exceed 35° C. and the start mix is diluted with water such that less than 33% tomato solids are in the start mix,
   separating a water soluble fraction from the solids of the tomato by a procedure that does not raise the temperature of the water soluble tomato fraction above 60° C. to yield a water soluble tomato fraction,
   filtration of the water soluble tomato fraction to remove particles larger than 1000 Daltons to yield a filtered water soluble tomato fraction,
   removal of free sugars from the filtered water soluble tomato fraction,
   wherein the dietary nitrate is extracted from a plant selected from the group consisting of Swiss chard, rocket, spinach, rhubarb, strawberry and lettuce,
   wherein the post exercise muscle soreness is effectively treated in the human in need thereof.

2. The method of claim 1, wherein the composition is in a form selected from the group consisting of a gel, dispersable tablet, powder, drink, and food.

3. The method of claim 1, wherein the human exercises at an intensity corresponding to greater than approximately 60% $VO_2$ max.

4. The method of claim 1, wherein the therapeutically effective amount of the dietary nitrate is between 25 mg and 250 mg.

* * * * *